United States Patent
Haight et al.

(10) Patent No.: US 9,808,356 B2
(45) Date of Patent: Nov. 7, 2017

(54) KNEE BALANCING DEVICES, SYSTEMS AND METHODS

(71) Applicant: Synvasive Technology, Inc., El Dorado Hills, CA (US)

(72) Inventors: Michael Haight, Sacramento, CA (US); Kenneth D Johannaber, Rancho Murieta, CA (US)

(73) Assignee: Synvasive Technology, Inc., El Dorado Hills, CA (US)

( * ) Notice: Subject to any disclaimer, the term of this patent is extended or adjusted under 35 U.S.C. 154(b) by 426 days.

(21) Appl. No.: 13/659,280

(22) Filed: Oct. 24, 2012

(65) Prior Publication Data

US 2013/0102929 A1    Apr. 25, 2013

Related U.S. Application Data

(60) Provisional application No. 61/550,766, filed on Oct. 24, 2011.

(51) Int. Cl.
*A61F 2/46*     (2006.01)
*A61B 17/02*    (2006.01)

(52) U.S. Cl.
CPC .......... *A61F 2/4657* (2013.01); *A61B 17/025* (2013.01); *A61B 2017/0268* (2013.01);
(Continued)

(58) Field of Classification Search
CPC ................ A61B 17/025; A61B 5/4528; A61B 2017/0268
(Continued)

(56) References Cited

U.S. PATENT DOCUMENTS

| | | | |
|---|---|---|---|
| 2004/0097951 A1* | 5/2004 | Steffensmeier | A61B 5/107 606/102 |
| 2010/0023067 A1 | 1/2010 | DiSilvestro et al. | |

(Continued)

FOREIGN PATENT DOCUMENTS

| | | |
|---|---|---|
| EP | 1304093 A1 | 4/2003 |
| EP | 2138107 A1 | 12/2009 |
| WO | WO-2013063043 A1 | 5/2013 |

OTHER PUBLICATIONS

"International Application Serial No. PCT/US2012/061588, International Preliminary Report on Patentability dated Oct. 21, 2013", 6 pgs.
(Continued)

*Primary Examiner* — Jeffrey G Hoekstra
*Assistant Examiner* — Yasmeen S Warsi
(74) *Attorney, Agent, or Firm* — Schwegman Lundberg & Woessner, P.A.

(57) ABSTRACT

Devices, systems and methods are provided for facilitating knee balancing during a knee replacement surgery. A system can include a force sensor, a main body, a moveable sensor platform, and an adjustment mechanism. The force sensor can sense one or more forces applied within a knee joint, including forces applied on a medial side and a lateral side. The movable sensor platform can be coupled between the force sensor and the main body. The adjustment mechanism can adjust the moveable sensor platform, relative to the main body, thereby adjusting a collective height of the system. A method can include inserting portions of a knee balancing system into a gap formed between a cut distal end of a femur and a cut proximal end of a tibia, adjusting an adjustable mechanism of the system to increase or decrease a collective system height, and sensing and displaying the medial and lateral forces.

24 Claims, 18 Drawing Sheets

(52) U.S. Cl.
 CPC ............... *A61F 2002/4658* (2013.01); *A61F 2002/4661* (2013.01); *A61F 2002/4666* (2013.01)

(58) Field of Classification Search
 USPC ........................................................ 600/587
 See application file for complete search history.

(56) References Cited

U.S. PATENT DOCUMENTS

| | | |
|---|---|---|
| 2010/0198275 A1* | 8/2010 | Chana et al. ............... 606/86 R |
| 2010/0249658 A1 | 9/2010 | Sherman |
| 2010/0249787 A1 | 9/2010 | Roche |
| 2010/0249791 A1* | 9/2010 | Roche ............................ 606/90 |

OTHER PUBLICATIONS

"International Application Serial No. PCT/US2012/061588, International Search Report dated Jan. 3, 2013", 10 pgs.
"International Application Serial No. PCT/US2012/061588, Written Opinion dated Jan. 3, 2013", 8 pgs.

* cited by examiner

KNEE BALANCING DEVICES, SYSTEMS AND METHODS

CLAIM OF PRIORITY

This non-provisional patent application claims the benefit of priority under 35 U.S.C. §119(e) to U.S. Provisional Patent Application Ser. No. 61/550,766, entitled "KNEE BALANCING SYSTEM AND METHOD," filed on Oct. 24, 2011, which is hereby incorporated by reference in its entirety. This non-provisional patent application further claims the benefit of priority under 35 U.S.C. §120 to U.S. patent application Ser. No. 12/609,666, entitled "FORCE SENSING DISTAL FEMORAL ALIGNMENT SYSTEM AND METHOD OF USE," filed on Oct. 30, 2009.

TECHNICAL FIELD

This patent document relates generally to surgical devices, systems and methods. More specifically, but not by way of limitation, this patent document relates to devices, systems and methods for facilitating knee surgical procedures, such as knee replacement procedures.

BACKGROUND

Knee arthritis is a debilitating problem that is increasing in prevalence due to an aging population and an obesity epidemic in much of the world. In an arthritic knee, protective cartilage at a point of articulation between a femur and a tibia is often worn away, diseased or otherwise damaged, causing significant pain, discomfort, and disability for a human subject. In many cases, knee arthritis leads human subjects to seek knee replacement surgery, also referred as "knee arthroplasty." Nearly 600,000 knee replacement surgeries are performed annually in the U.S. alone.

Knee arthroplasty involves replacing one or more worn, diseased or otherwise damaged knee joint surfaces with metal and/or plastic components shaped to allow natural motion of the knee. Knee replacement can be total or partial. Total knee replacement surgery, also referred to as total knee arthroplasty ("TKA"), involves a total replacement of a distal end of a femur, a proximal end of a tibia, and often an inner surface of a patella with prosthetic parts. Cuts are made on the distal end of the femur, the proximal end of the tibia, and optionally, the inner surface of the patella. Prosthetic parts are then attached to the cut surfaces. The prosthetic parts are intended to create a stable knee joint that moves through a normal range of motion. The replacement of knee structures with prosthetic parts can, if appropriately implanted, allow the knee to avoid bone-on-bone contact and provide smooth, well-aligned surfaces for joint movement.

OVERVIEW

The present inventors recognize, among other things, that one of the most important aspects of a successful TKA procedure is ensuring that ligament or soft tissue tension is balanced on both sides of a knee joint. Four ligaments can be important in the proper functioning of a knee—the anterior cruciate ligament, the posterior cruciate ligament, the medial collateral ligament, and the lateral collateral ligament. Ideally, there should be approximately equal ligament or soft tissue tension on a medial side of the knee joint and on a lateral side of the knee joint once the prosthetic knee is implanted. If there is ligament or soft tissue imbalance, the prosthetic knee will often not work properly, not feel right, and/or wear unevenly, potentially resulting in another knee replacement in just a few years' time. Typically, ligament or soft tissue balancing during a TKA procedure is done through approximation by an attending surgeon or other caregiver, often using multiple shims inserted between the distal femur and proximal tibia during the procedure to approximate an ideal tension balance. Such approximations require a great deal of experience and skill, and if done improperly, the results of the TKA procedure can be significantly compromised.

As such, the present inventors recognize that there is a need for devices, systems and methods configured to facilitate knee balancing during a TKA procedure, for example. The devices, systems and methods can be configured to help an attending surgeon or other caregiver estimate ligament or soft tissue tension on medial and lateral sides of the knee so that ligament release(s) can be performed as necessary. The devices, systems and methods can be configured to be relatively simple to use and nonintrusive upon the rest of the TKA procedure.

Devices, systems and methods are provided for facilitating knee balancing during a knee replacement surgery. A system can include a force sensor, a main body, a moveable sensor platform, and an adjustment mechanism. The force sensor can sense one or more forces applied within a knee joint, including forces applied on a medial side and a lateral side. The movable sensor platform can be coupled between the force sensor and the main body. The adjustment mechanism can adjust the moveable sensor platform, relative to the main body, thereby adjusting a collective height of the system. A method can include inserting portions of a knee balancing system into a gap formed between a distal end of a femur and a proximal end of a tibia, adjusting an adjustable mechanism of the knee balancing system to increase or decrease a collective height of the system, and sensing and displaying the medial and lateral forces.

To better illustrate the knee balancing devices, systems and methods disclosed herein, a non-limiting list of examples is provided here:

In Example 1, a knee balancing system for facilitating a knee arthroplasty procedure comprises a force sensor configured to sense one or more forces applied within a knee joint, including a force applied on a medial side of the knee joint and a force applied on a lateral side of the knee joint; a main body; a moveable sensor platform, coupled between the force sensor and the main body; and an adjustment mechanism configured to adjust the moveable sensor platform relative to the main body.

In Example 2, the system of claim 1 is optionally configured such that the force sensor is configured to sense one or more forces applied within the knee joint between a cut distal end of a femur and a cut proximal end of a tibia.

In Example 3, the system of any one or any combination of Examples 1 or 2 optionally further comprises a numerical display, wirelessly or integrally coupled with the force sensor, configured to display a first number representing the force applied on the medial side and a second number representing the force applied on the lateral side.

In Example 4, the system of any one or any combination of Examples 1-3 is optionally configured such that movement of the adjustment mechanism results in the moveable sensor platform moving up or down, relative to the main body, to respectively increase or decrease a height of portions of the force sensor that reside within the knee joint, relative to the main body.

In Example 5, the system of Example 4 is optionally configured such that a collective height of portions of the force sensor, the main body, the moveable sensor platform, and the adjustable mechanism that reside within the knee joint is adjustable from about 15 millimeters to about 21 millimeters.

In Example 6, the system of any one or any combination of Examples 1-5 is optionally configured such that one or both of the movable sensor platform or the adjustment mechanism includes a plurality of height markings.

In Example 7, the system of any one or any combination of Examples 1-6 is optionally configured such that the main body includes a platform configured to be inserted into the knee joint and couple with the moveable sensor platform; a shaft extending from the platform; and a handle at an end of the shaft, opposite the platform.

In Example 8, the system of Example 7 is optionally configured such that the shaft extends from a location that is offset from a center of the platform.

In Example 9, the system of any one or any combination of Examples 1-8 is optionally configured such that the adjustment mechanism includes one or more threaded screws or bolts.

In Example 10, the system of Example 9 is optionally configured such that the adjustment mechanism further includes an adjustable wedge movable within a perimeter of the main body through rotation of the one or more threaded screws or bolts.

In Example 11, the system of Example 10 is optionally configured such that the adjustable wedge includes a base member, one or more plate members, and one or more column members, the one or more plate members are moveable within the perimeter of the main body through rotation of the one or more threaded screws or bolts.

In Example 12, the system of Example 11 is optionally configured such that the one or more column members move along a first planar direction when the one or more plate members move along a second planar direction, which is perpendicular to the first planar direction.

In Example 13, the system of any one or any combination of Examples 9-12 is optionally configured such that the adjustment member further includes a screwdriver or a wrench.

In Example 14, the system of any one or any combination of Examples 1-13 is optionally configured such that the adjustment mechanism includes one or more actuating ramped surfaces configured to adjust the moveable sensor platform relative to the main body.

In Example 15, the system of Example 14 is optionally configured such that the moveable sensor platform includes one or more actuating ramped surfaces that engage with the one or more actuating ramped surfaces of the adjustment mechanism.

In Example 16, a method for facilitating balancing tension applied to a knee joint by one or more ligaments or other soft tissue during a knee arthroplasty procedure comprises inserting portions of a knee balancing system, including a force sensor, a main body, a movable sensor platform coupled between the force sensor and the main body, and an adjustment mechanism, into a gap formed between a distal end of a femur and a proximal end of a tibia; adjusting the adjustable mechanism of the knee balancing system to increase or decrease a collective height of the system, including moving the moveable sensor platform and the force sensor relative to the main body; sensing, using the force sensor, an amount of medial force applied against a medial portion of the knee balancing system by the femur and the tibia and an amount of lateral force applied against a lateral portion of the knee balancing system by the femur and the tibia; and displaying the amounts of medial and lateral force on the knee balancing system.

In Example 17, the method of Example 16 optionally further comprises releasing at least one ligament or soft tissue structure of the knee joint based on the displayed amounts of medial and lateral force.

In Example 18, the method of any one or any combination of Examples 16 or 17 is optionally configured such that inserting the portions of the knee balancing system into the gap formed between the distal end of the femur and the proximal end of the tibia includes inserting the portions of the knee balancing system between a cut surface of the distal end of the femur and a cut surface of the proximal end of the tibia.

In Example 19, the method of any one or any combination of Examples 16-18 is optionally configured such that adjusting the adjustable mechanism of the knee balancing system includes increasing the collective height of the system from about 15 millimeters to at least about 17 millimeters.

In Example 20, the method of any one or any combination or Examples 16-19 is optionally configured such that adjusting the adjustable mechanism of the knee balancing system includes engaging one or more threads of a screw or a bolt with an adjustable wedge including one or more actuating ramped surfaces.

In Example 21, the method of Example 20 is optionally configured such that engaging the one or more threads of the screw or the bolt with the adjustable wedge includes turning a wrench or a screwdriver coupled with the screw or bolt.

In Example 22, the method of any one or any combination of Examples 16-21 is optionally configured such that adjusting the adjustable mechanism of the knee balancing system includes engaging one or more threads of a first screw or first bolt with a first plate member and engaging one or more threads of a second screw or second bolt with a second plate member.

In Example 23, the method of Example 22 is optionally configured such that engaging the one or more threads of the first screw or first bolt with the first plate member includes adjusting the collective height of the medial portion of the knee balancing system, and wherein engaging the one or more threads of the second screw or second bolt with the second plate member includes adjusting the collective height of the lateral portion of the knee balancing system.

In Example 24, the method of any one or any combination of Examples 16-23 is optionally configured such that displaying the amounts of medial and lateral force includes displaying a first numerical value representing an amount of force applied against the medial portion of the knee balancing system and a second numerical value representing an amount of force applied against the lateral portion of the knee balancing system.

In Example 25, the knee balancing device, system, or method of any one (or portion or one) or any combination of Examples 1-24 is optionally configured such that all elements or options recited are available to use or select from.

These and other examples and features of the present knee balancing devices, systems, or methods will be set forth in part in the following Detailed Description. This Overview is intended to provide non-limiting examples of the present subject matter—it is not intended to provide an exclusive or exhaustive explanation. The Detailed Description below is included to provide further information about the present knee balancing devices, systems and methods.

BRIEF DESCRIPTION OF THE DRAWINGS

In the drawings, like numerals can be used to describe similar elements throughout the several views. Like numerals having different letter suffixes can be used to represent different views or features of similar elements. The drawings illustrate generally, by way of example, but not by way of limitation, various embodiments discussed in the present document.

DETAILED DESCRIPTION

The present inventors recognize that there is a need for devices, systems and methods configured to facilitate knee balancing during a TKA procedure, as well as other procedures that can benefit through distraction from a thin profile. The devices, systems and methods can be configured to help an attending surgeon or other caregiver estimate ligament or soft tissue tension on medial and lateral sides of a knee, and optionally, the anterior and posterior sides of the knee so that appropriate ligament release(s) can be performed. In this way, a prosthetic knee joint can be more optimally implanted. The devices, systems and methods can be configured to be relatively simple to use and nonintrusive upon the rest of the TKA procedure.

Figure 1:
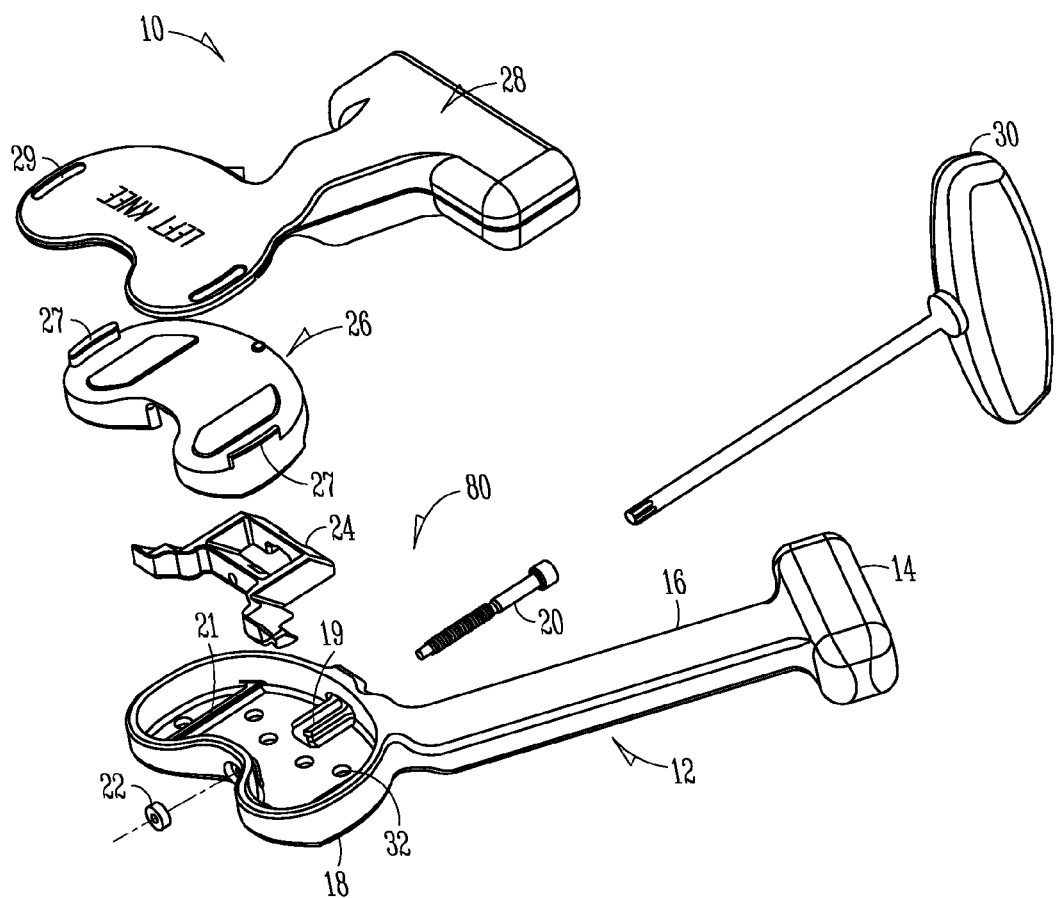
FIG. 1: illustrates an exploded view of a knee balancing system, as constructed in accordance with at least one embodiment.

FIG. 1 illustrates an example of a knee balancing system 10, as constructed in accordance with at least one embodiment of the present disclosure. The knee balancing system 10 can include a main body (or "stationary member") 12, an adjustable wedge 24, a force sensor 28, a moveable sensor platform 26 coupled between the force sensor 28 and the main body 12, and an adjustment wrench 30. The moveable sensor platform 26 can include one or more attachment members 27 for attaching with mating attachment members (e.g., voids) 29 on the force sensor 28.

Optionally, one or more of the knee balancing system 10 components can be sterilized, such as by autoclave, chemical sterilization, or the like, and thereafter reused. In varying examples, all components of the system 10 except the force sensor 28 can be sterilized and reused. It can be advantageous for patient safety to have the force sensor 28 configured as a disposable component of the system 10. To this end, the attachment members 27, 29 can be keyed to "talk" to each other (e.g., via a mechanical attachment mechanism, an electronic recognition system, or some combination of the two) enabling the system 10 to be configured such that no other force sensor, other than the force sensor 28 provided with the system 10, can be used. This prevents the use of inferior and potentially dangerous counterfeit, worn out, or insufficiently sterilized force sensors from being used. As an alternative to the attachment members 27, 29 talking to each other, the force sensor 28 can be programmed to work in one surgical procedure only and thereafter be permanently shut down or disabled.

The main body 12 can include a handle 14, a shaft 16, and a platform 18. The main body 12 can be made of any suitable material, such as but not limited to stainless steel, other metals, or polymers. In some examples, the platform 18 can include one or more drainage holes 32 to facilitate cleaning of the main body 12 and/or a general shape approximating a knee joint surface on which it is to be placed. The shaft 16, which extends from the platform 18, can be offset from the center of the platform 18. This offset configuration can facilitate inserting the platform 18 into a knee joint when the patella is moved off to one side of the joint. It can also facilitate adjusting the system 10 by leaving more room for accessing an adjustment screw 20. The handle 14 can have any suitable configuration for enhancing ergonomics and ease of use of the main body 12.

The platform 18 can include a track 19 and one or more guide rails 21. The adjustable wedge 24 can be attached to the platform 18, such as via the adjustment screw 20 and an adjustment screw capture nut 22, to ride over the track 19 and one or more guide rails 21. In this example, an adjustment mechanism 80 can include one or more of the adjustable wedge 24, the adjustment screw 20, the adjustment screw capture nut 22, and the adjustment wrench 30. The adjustment mechanism 80 can be configured to adjust the moveable sensor platform 26, relative to the main body 12, thereby adjusting a collective height of the system 10 (i.e., a distance from a surface of the system engagable with a cut distal femur to a surface of the system engagable with a cut proximal tibia).

When assembled, portions of the knee balancing system 10 can be advanced into a gap between the cut distal femur and the cut proximal tibia during knee replacement surgery. The adjustment wrench 30 can be used to adjust the collective height (or "thickness") of the system 10 portions residing in the gap. The collective height of the system 10 portions residing in the gap can, in some examples, range between about 15 millimeters and about 21 millimeters, inclusive. The collective height can be about 15 millimeters for insertion into the gap and, when fully expanded, be about 21 millimeters. As the collective height of the system 10 increases, the force sensor 28 can be used to sense forces applied by a medial part of the knee and a lateral part of the knee. Ligament release(s) can then be performed, if necessary, to balance the medial and lateral forces, after which time the system 10 can be removed and the knee replacement procedure completed.

Figure 2:
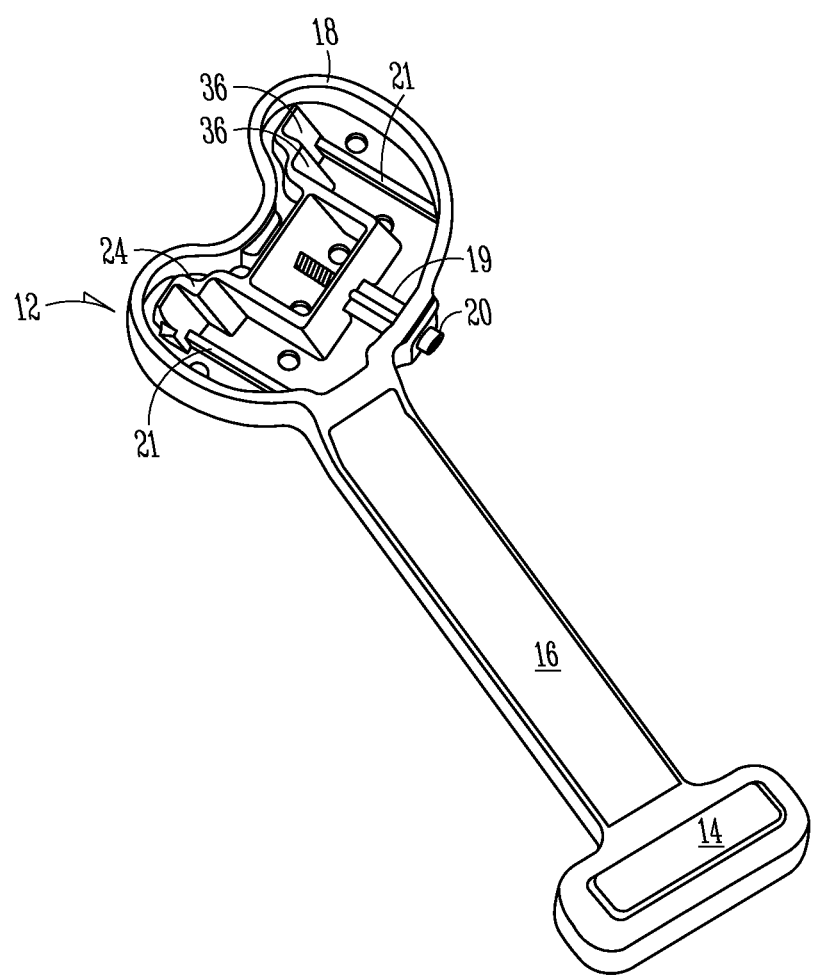
FIG. 2: illustrates an elevation view of a bottom side of a main body and an adjustment mechanism of a knee balancing system, as constructed in accordance with at least one embodiment.

FIG. 2 illustrates an elevation view of a bottom side of the main body 12 and the adjustable wedge 24. The adjustable wedge 24 is shown in place within the main body 12 and is attached via the adjustment screw 20. When the adjustment screw 20 is operated, the adjustable wedge 24 can move backward and/or forward within a perimeter of the platform 18, guided by the one or more guide rails 21 and the track 19.

Figure 3:
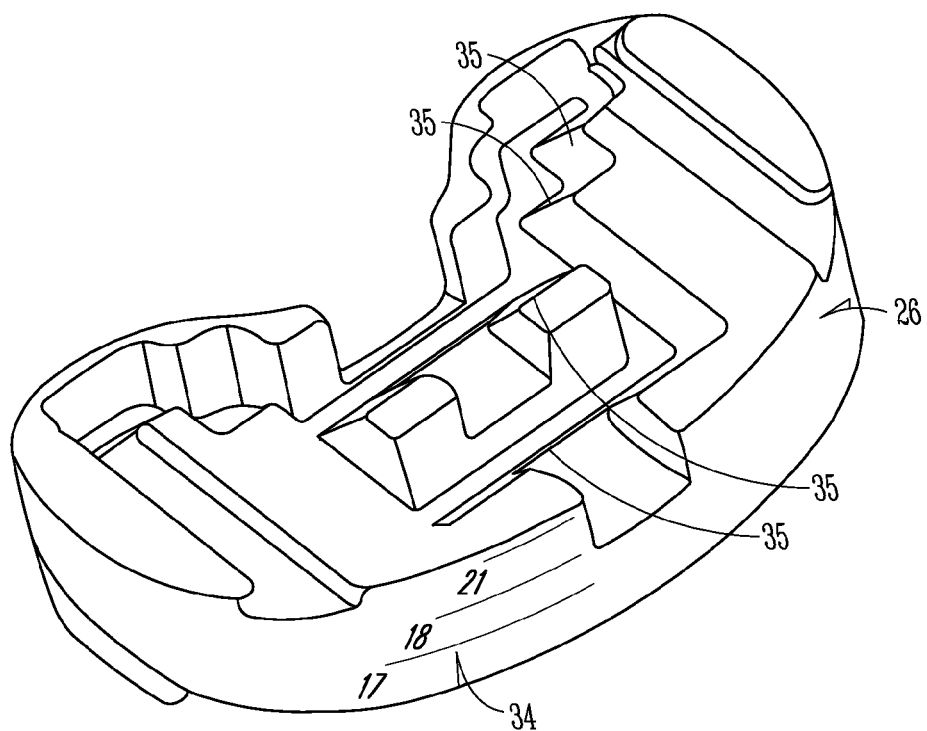
FIG. 3: illustrates an elevation view of a top side of a movable sensor platform of a knee balancing system, as constructed in accordance with at least one embodiment.

FIG. 3 illustrates an elevation view of a top side of the moveable sensor platform 26. As shown, the moveable sensor platform can have a general outer shape similar to that of the platform 18. The moveable sensor platform 26 can include graduated distraction height markings 34, such as on an outer surface, to indicate to an attending surgeon or other caregiver a current height of the gap between a patient's cut distal femur and cut proximal tibia. The height can, in some examples, be measured in increments of about 2 mm, from about 15 mm fully collapsed to about 21 mm when fully expanded. In alternative examples, other markings can be included on the moveable sensor platform 26, such as 1 mm incremental markings, various colored dots or lines with or without numbers, colored stripes or the like or, as shown in FIG. 5B, markings 34A can be included on a column member of an adjustment mechanism.

The moveable sensor platform 26 can include one or more actuating ramped surfaces 35 to mate with corresponding actuating ramped surfaces 36 (FIG. 2) on the adjustable wedge 24. By coupling the moveable sensor platform 26 between the adjustable wedge 24 (FIG. 1) and the force sensor 28 (FIG. 1), the moveable sensor platform 26 can adjust the collective height of the system 10 portions that fit into the gap between the cut distal femur and the cut proximal tibia. Optionally, the force sensor 28 and the moveable sensor platform 26 can be combined as a single piece.

Figure 4:
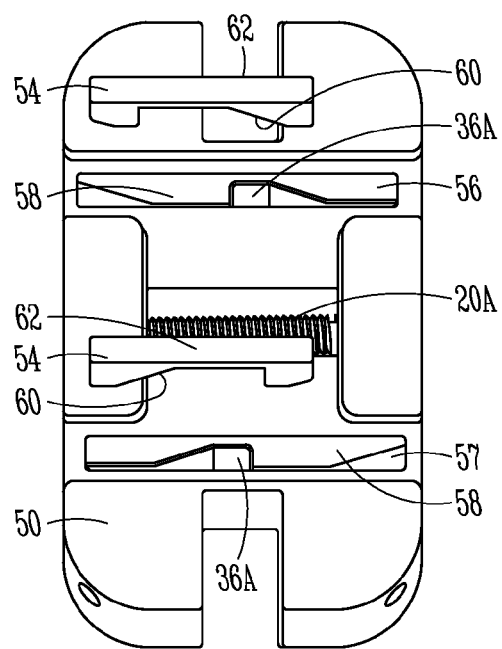
FIGS. 4, 7, 10, and 13: illustrate an elevation exploded view of a bottom side of portions of an adjustment mechanism of a knee balancing system, as constructed in accordance with various embodiments.
Figure 5A:
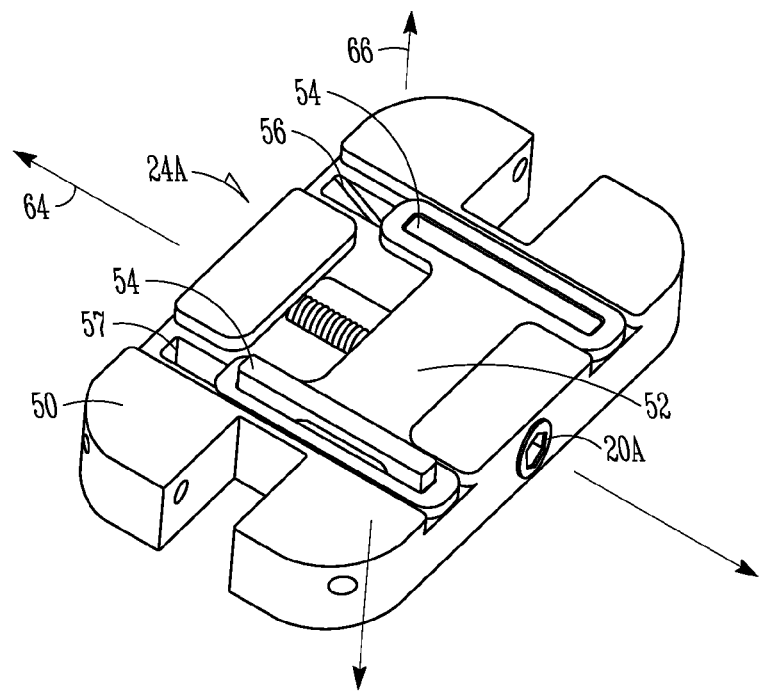
FIGS. 5A-5B, 8A-8B, 11, and 14: illustrate an elevation view of a bottom side of an adjustment mechanism of a knee balancing system, as constructed in accordance with various embodiments.
Figure 5B:
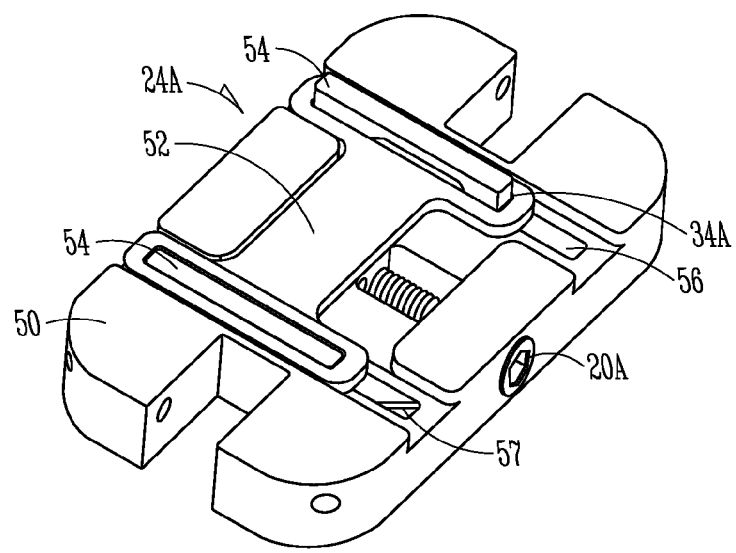
Figure 6:
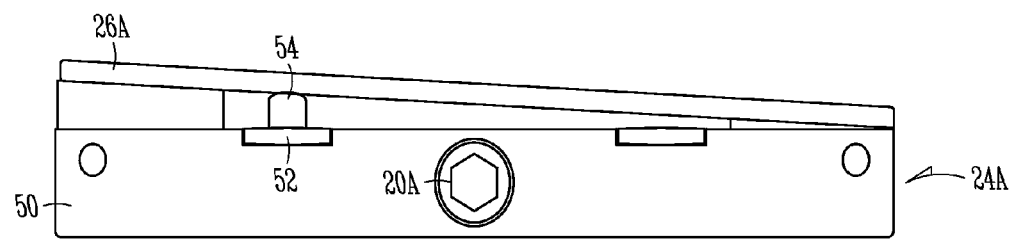
FIGS. 6, 9, 12, and 15: illustrate a front assembled view of an adjustment mechanism and a movable sensor platform, as constructed in accordance with various embodiments.
Figure 7:
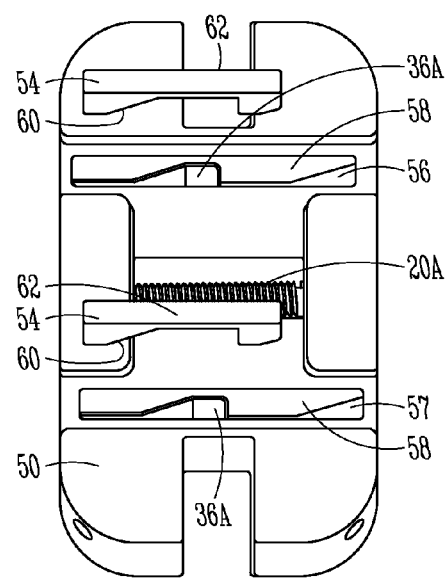
Figure 8A:
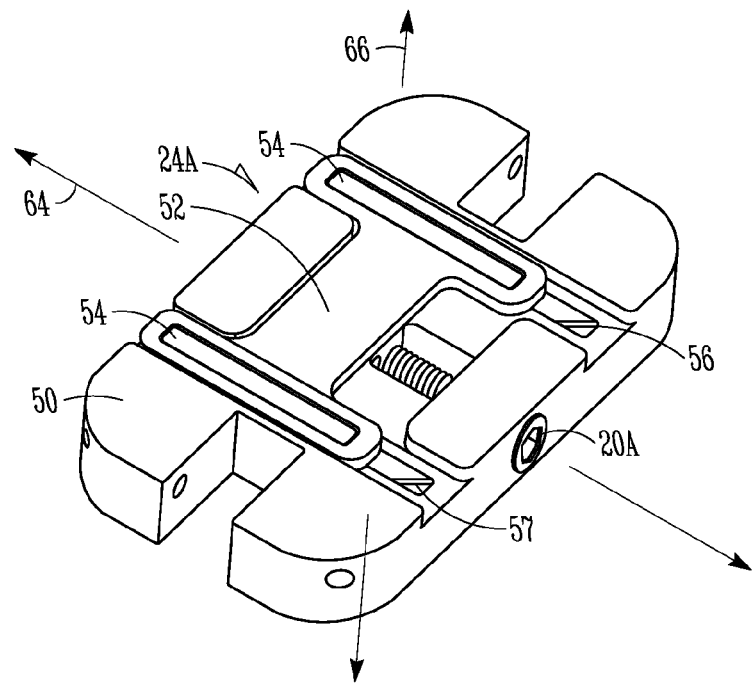
Figure 8B:
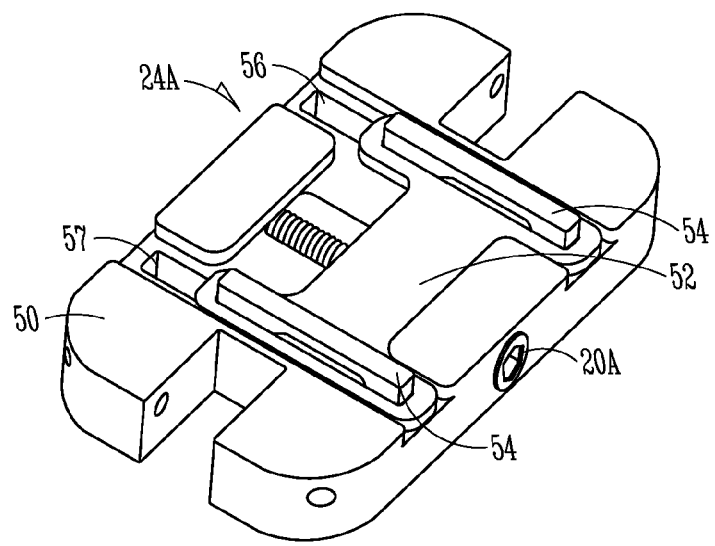
Figure 9:
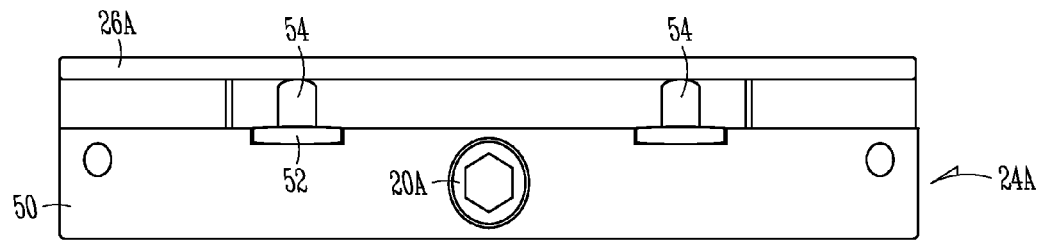
Figure 10:
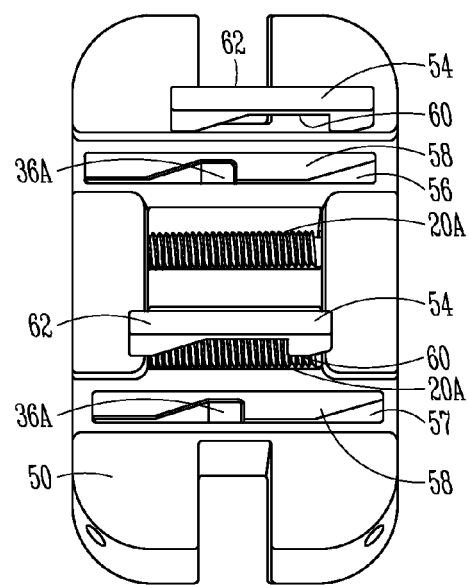
Figure 11:
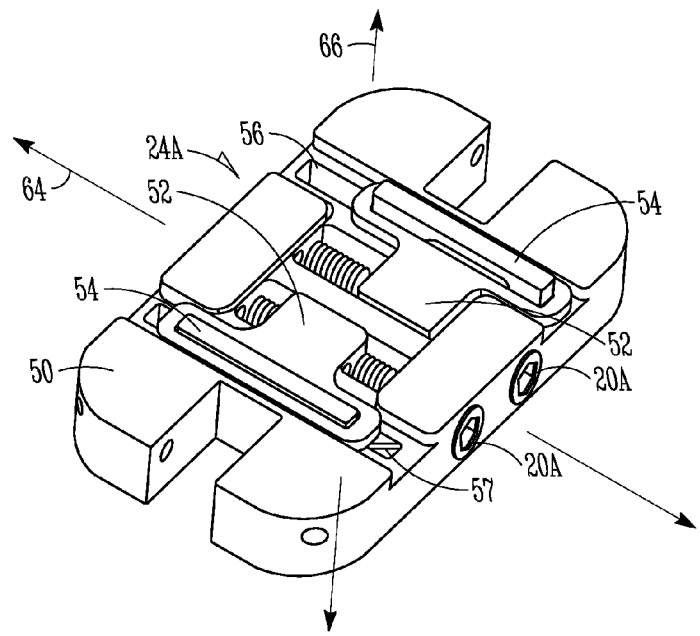
Figure 12:
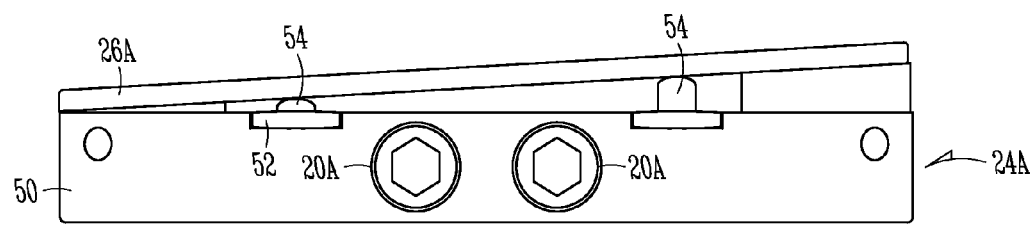
Figure 13:
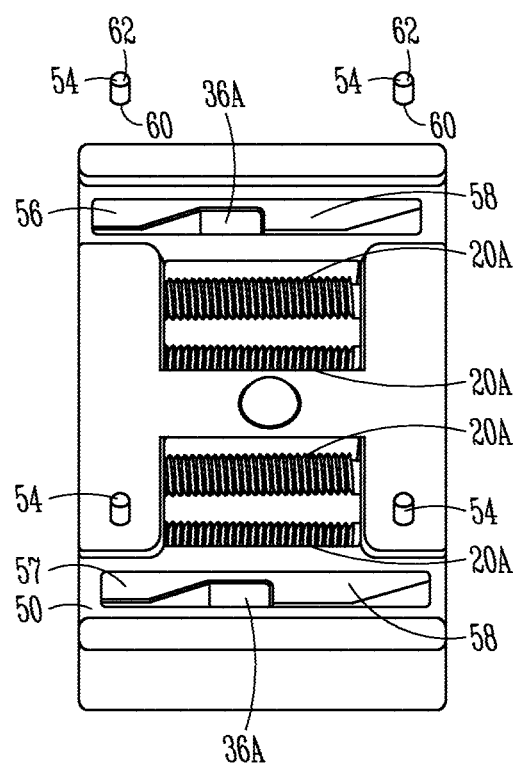
Figure 14:
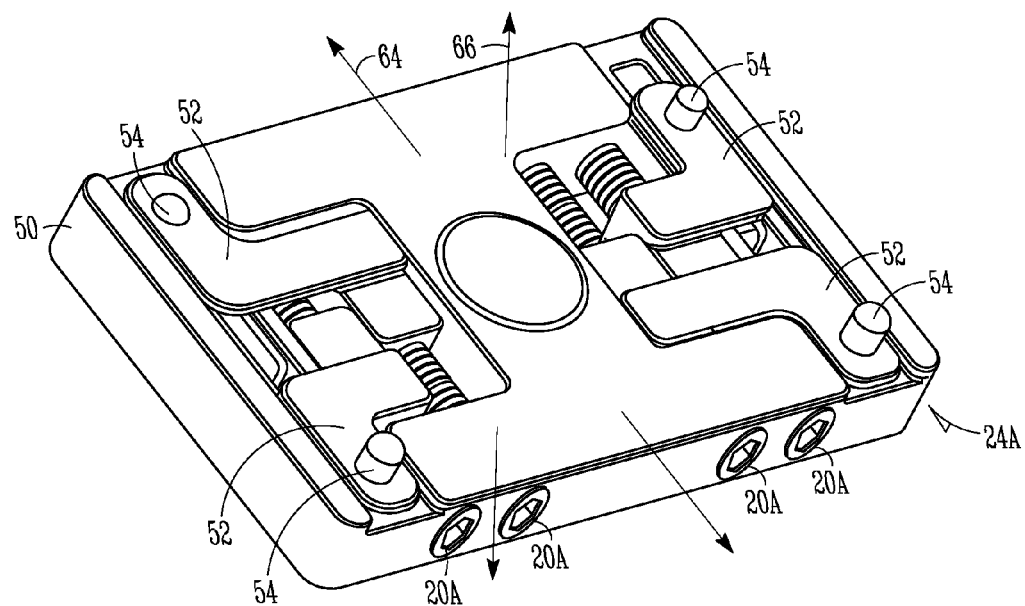
Figure 15:
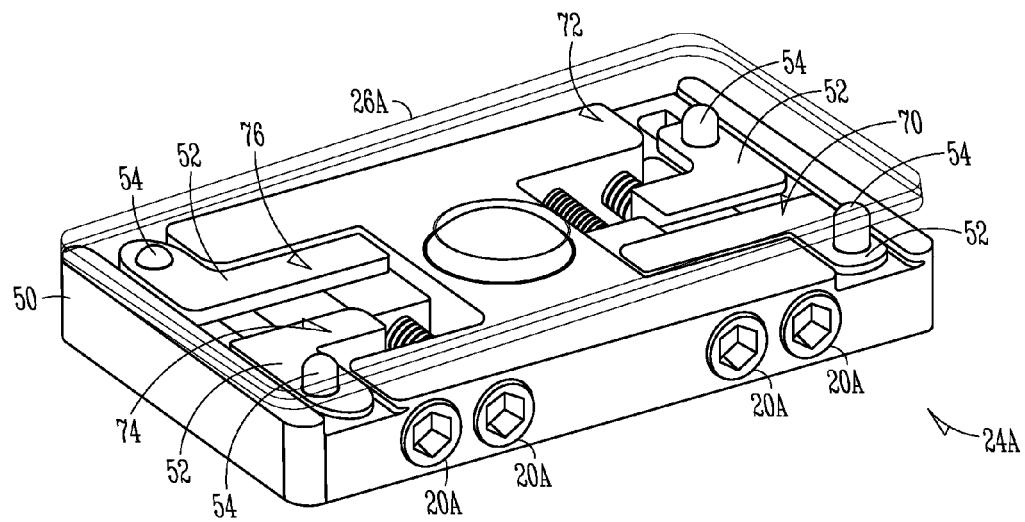

FIGS. 4-15 illustrate alternative examples of an adjustment mechanism for use in knee balancing systems, such as the knee balancing system 10 shown in FIG. 1. More specifically, FIGS. 4-6 illustrate a first alternative example of an adjustment mechanism; FIGS. 7-9 illustrate a second alternative example of an adjustment mechanism; FIGS. 10-12 illustrate a third alternative example of an adjustment mechanism; and FIGS. 13-15 illustrate a fourth alternative example of an adjustment mechanism. Optionally, it is believed that a distal cut guide can be coupled to one or more of these alternative adjustment mechanisms if, for example, an attending surgeon or other caregiver favors soft tissue guided alignment.

Each of the adjustment mechanism alternatives can include, among other things, an adjustable wedge 24A and one or more adjustment screws 20A. The adjustable wedge 24A can include a base member 50, one or more plate members 52, and one or more column members 54. Each base member 50 can include a medial track 56 and a lateral track 57 within which the one or more column members 54 can travel, under the direction of the one or more plate members 52. The medial 56 and lateral 57 tracks can each include one or more actuating ramped surfaces 36A and one or more dead (or neutral) areas 58. When a hidden surface 60 of the one or more column members 54 contacts the one or more actuating ramped surfaces 36A and the one or more dead areas 58, an exposed surface 62 of the column members 54 changes (e.g., increases or decreases) in height and remains fixed at a neutral height, respectively. An increase in height of the exposed surface 62 can cause adjacent portions of a moveable sensor platform 26A to move up relative to (or away from) a main body (see, e.g., the main body 12 of FIG. 1), thereby increasing a collective height of a knee balancing system 10. Conversely, a decrease in height of the exposed surface 62 can cause adjacent portions of the moveable sensor platform 26A to move closer to the main body. A fixing in height of the exposed surface 62, by way of the one or more dead areas 58, can cause adjacent portions of the moveable sensor platform 26A to remain fixed or neutral relative to the main body.

In varying examples, the one or more column members 54 are coupled to the one or more plate members 52 and move when the plate members 52 move. The one or more plate members 52 can be movable within a perimeter of the main body through rotation of the one or more adjustment screws 20A, such as via an adjustment wrench (see, e.g., the adjustment wrench 30 of FIG. 1). In the examples of FIGS. 4-15, movement of the one or more plate members 52 along a substantially horizontal planar direction 64 causes the one or more column members 54 to move or remain fixed along a substantially vertical planar direction 66.

In the example of FIGS. 4-6 (also referred to a dual side, opposing lift example using a single adjustment screw), a base member 50 can include a medial track 56 and a lateral track 57, each track having actuating ramped surfaces 36A and dead areas 58 that are mirror images of one another. Similarly, a hidden surface 60 associated with a medial column member 54 is oriented opposite (or mirror) a hidden surface 60 associated with a lateral column member 54. As a result, movement of a plate member 52 along a substantially horizontal planar direction 64, generated by rotation of a single adjustment screw 20A, causes a height of an exposed surface 62 of one of the medial or lateral column members 54 to change, relative to a main body and along a substantially vertical planar direction 66, while a height of the other column member's exposed surface 62 remains fixed at a neutral height, relative to the main body.

In the example of FIGS. 7-9 (also referred to as a dual side, single lift example using a single adjustment screw), a base member 50 can include identical medial 56 and lateral 57 tracks (i.e., tracks having actuating ramped surfaces 36A and dead areas 58 in identical locations within the base) and identically-oriented medial and lateral column members 54. As a result, movement of a plate member 52 along a substantially horizontal planar direction 64, generated by rotation of a single adjustment screw 20A, causes a height of an exposed surface 62 of each of medial and lateral column members 54 to change or remain fixed at a neutral height, relative to a main body and along a substantially vertical planar direction 66, together.

In the example of FIGS. 10-12 (also referred to as a dual side, dual lift example using two adjustment screws), a base member 50 can include identical medial 56 and lateral 57 tracks (i.e., tracks having actuating ramped surfaces 36A and dead areas 58 in identical locations within the base) and identically-oriented medial and lateral column members 54. However, unlike the example of FIGS. 7-9, this example includes two plate members 52 and two adjustment screws 20A. As a result, a height of an exposed surface 62 of a column member associated with the medial track 56 can be independently adjusted from a height of an exposed surface 62 of a column member associated with the lateral track 57, even though the base member 50 includes identical medial 56 and lateral 57 tracks and the medial and lateral column members 54 are identically-oriented.

In the example of FIGS. 13-15 (also referred to as a quadrant lift example using four adjustment screws), a base member 50 can include identical medial 56 and lateral 57 tracks (i.e., tracks having actuating ramped surfaces 36A and dead areas 58 in identical locations within the base) and identically-oriented medial and lateral column members 54. However, unlike the example of FIGS. 10-12, this example includes two plate members 52 and two adjustment screws 20A associated with each of the medial 56 and lateral 57 tracks. As a result, a height of an exposed surface 62 of a column member 54 associated with each quadrant (e.g., an anterior/medial quadrant 70, a posterior/medial quadrant 72, an anterior/lateral quadrant 74, and a posterior/lateral quadrant 76) of the adjustment mechanism can be independently controlled.

Figure 16:
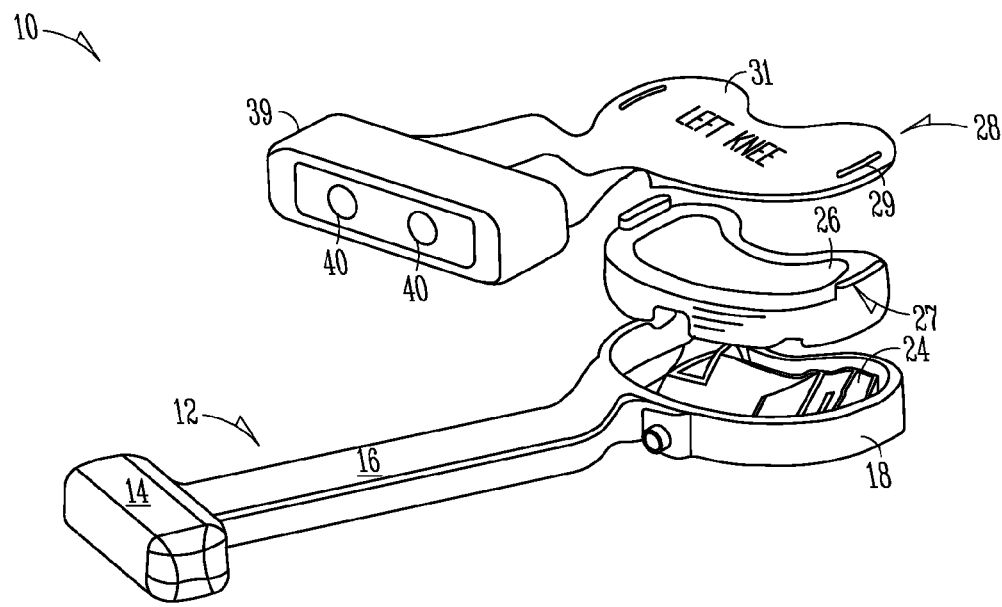
FIG. 16: illustrates an exploded view of a main body coupled with an adjustment mechanism, a movable sensor platform, and a force sensor of a knee balancing system, as constructed in accordance with at least one embodiment.
Figure 17:
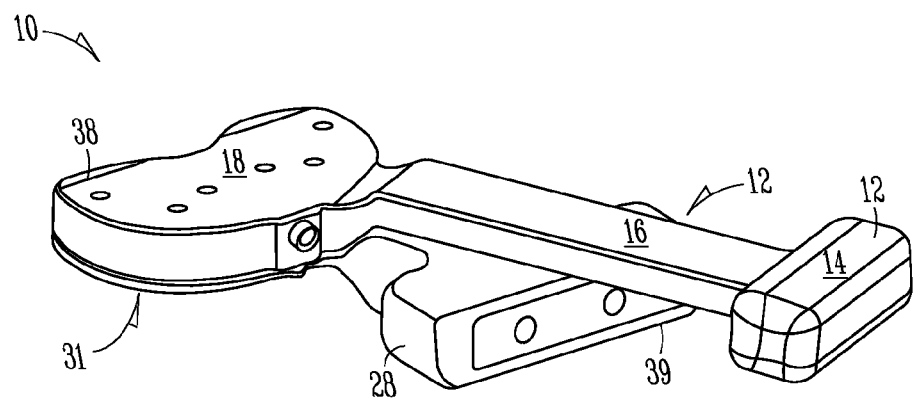
FIG. 17: illustrates an assembled view of a main body, an adjustment mechanism, a movable sensor platform, and a force sensor of a knee balancing system, as constructed in accordance with at least one embodiment.

FIGS. 16 and 17 respectively illustrate exploded and assembled views of a knee balancing system 10, such as the system 10 illustrated in, and described with reference to, FIGS. 1-3. The knee balancing system 10 can include the main body 12, the adjustable wedge 24, the moveable sensor platform 26, and the force sensor 28.

The force sensor 28 can generally include a platform portion 31 and a display portion 39, the latter including indicators 40 to indicate an amount of medial force and an amount of lateral force within a knee joint. Alternatively, the display portions 39 can be separate from the force sensor 28, but communicate with the force sensor 28 through wireless means. The platform portion 31 can include any suitable device for sensing force within the gap formed between the cut distal femur and the cut proximal tibia. For example, the platform portion 31 can include one sensor that is able to sense relative forces applied to medial and lateral sides of the knee joint. The platform portion 31 can include two sensors, one on each of the medial and lateral sides, for sensing force on the medial and lateral aspects of the knee joint.

The display portion 39 can include at least one and typically two indicators 40 to indicate to an attending surgeon or other caregiver an amount (or relative comparison) of force sensed at medial and lateral sides of the knee joint. Since indicators 40 and the numbers displayed can be used for comparison purposes (e.g., an amount of medial force vs. an amount of lateral force), any suitable numbers or indicators can be used that allow the attending surgeon or other caregiver to assess whether the knee is balanced or imbalanced. In the example shown, two LED indicators 40 can each display a number ranging from 0 to 20, representing a comparative amount of sensed force on the medial and lateral sides. If the two displayed numbers are equal, then the sensed forces are balanced. If the numbers are unequal, then the sensed forces are unbalanced. By way of example, but not of limitation, the numbers can equate to about 20 N of force per unit of 1 (for example, the number 2 would indicate 40 N).

The force sensor 28 can include any suitable type of sensor (or sensors), such as but not limited to piezoelectric sensors, force sensing resistors, strain gauges, load cells, other pressure sensors, and other force sensors. In one example, a known voltage is transmitted to sensors, the voltage passing out of sensors is measured, and a percentage of the voltage leaving sensors to the known voltage is calculated. From this percentage, a force can be derived. An analog signal representing the force can be converted to a digital signal with an analog-to-digital (A/D) converter, and the A/D converter can provide the digital signal to a look-up table that determines a display value (or values) representing the force (or forces). An attending surgeon or other caregiver can use the displayed value(s) as an absolute number and/or can move the knee joint and compare force values at flexion and extension. The A/D converter, as well as any additional processing modules for processing the sensed data into usable data, can be housed within the force sensor 28.

The force sensor 28 can be used in a right knee joint, a left knee joint, or both, during any given procedure. The force sensor 28 can be used to measure forces in a first knee joint and simply be flipped over to measure the forces in the opposite knee joint. Alternatively, knee-specific force sensors 28 can be provided.

Referring specifically to FIG. 17, the main body 12 can optionally include a chamfer 38 on its front or anterior aspect. The chamfer 38 can facilitate inserting the system 10 into the gap between a cut distal femur and a cut proximal tibia.

Figure 18:
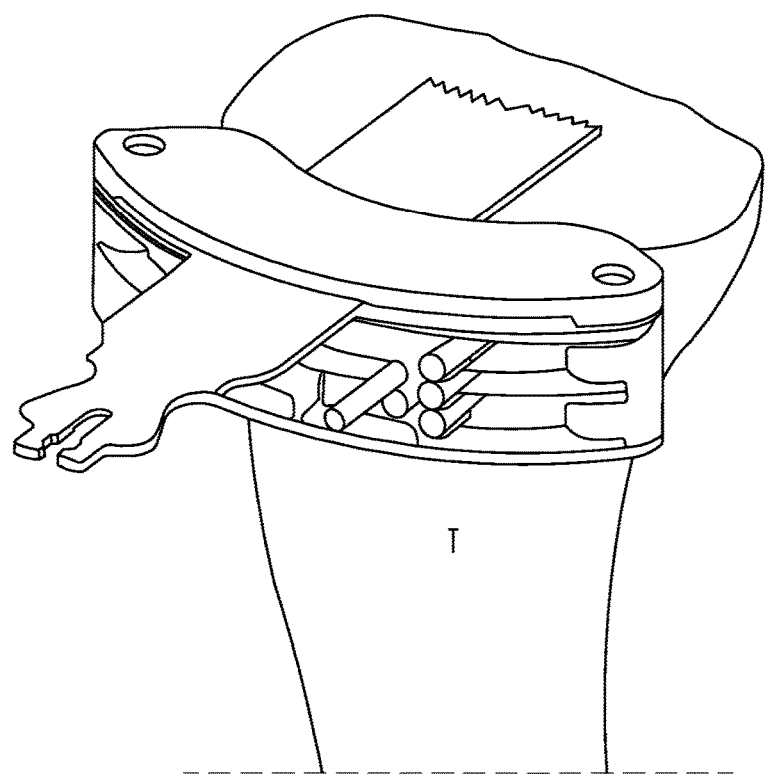
FIG. 18: illustrates a perspective view of cutting a proximal end of a tibia, as constructed in accordance with at least one embodiment.
Figure 19:
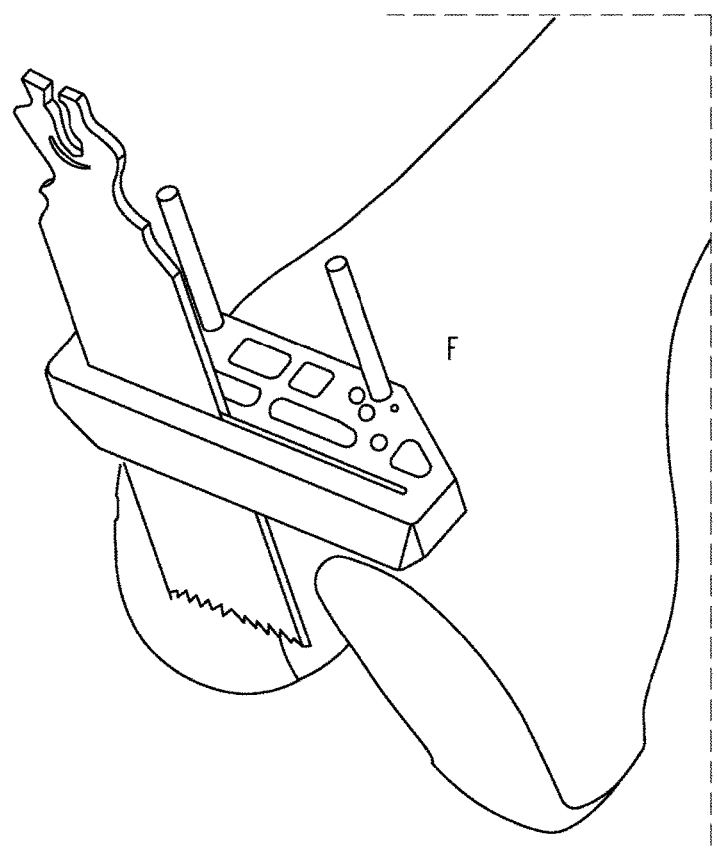
FIG. 19: illustrates a perspective view of cutting a distal end of a femur, as constructed in accordance with at least one embodiment.
Figure 20:
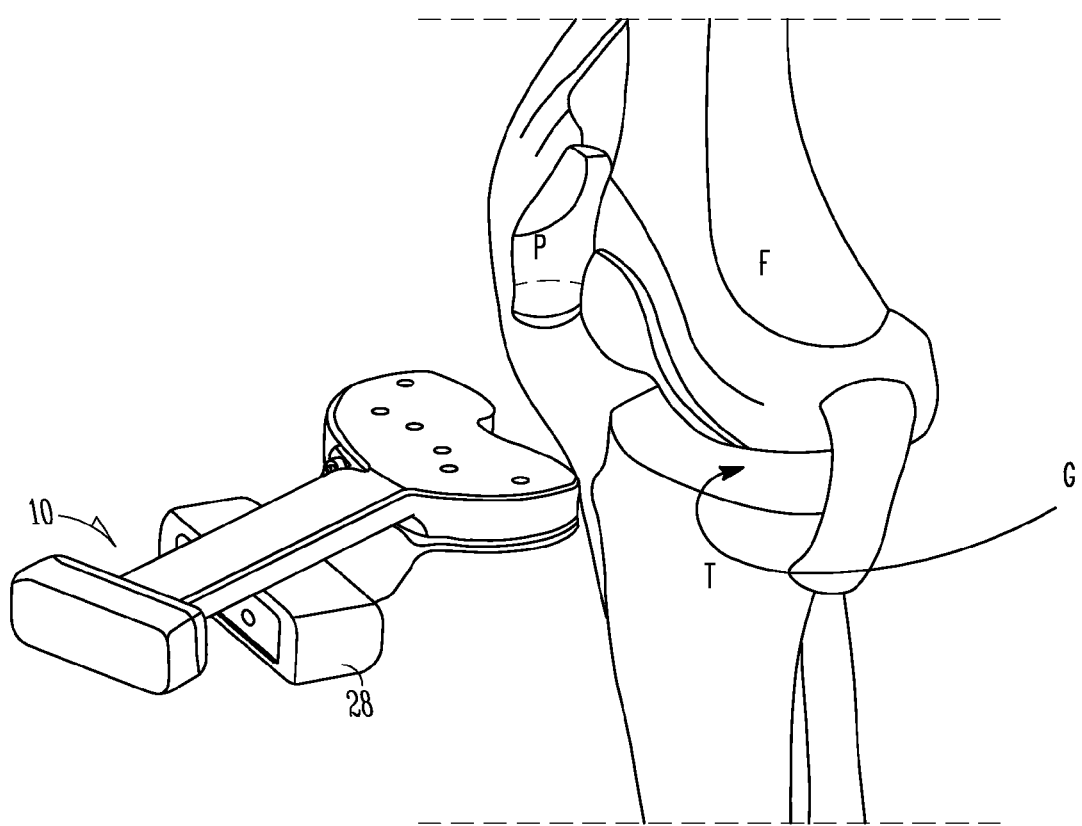
FIG. 20: illustrates a perspective view of inserting a knee balancing system into a gap formed between a cut surface on a distal end of a femur and a cut surface on a proximal end of a tibia, as constructed in accordance with at least one embodiment.

FIGS. 18-24 pictorially illustrate a method for balancing a knee joint during a knee surgical procedure. As shown in FIGS. 18 and 19, cuts can be made to a proximal tibia T and a distal femur F using any suitable bone cutting technique(s). These cuts create a gap G between the two opposing bone knee joint surfaces. As shown in FIG. 20, a patella P can be moved aside and a knee balancing system 10 can inserted, in its collapsed ("thin") configuration, into the gap G between the cut distal femur F and the cut proximal tibia T.

Figure 21:
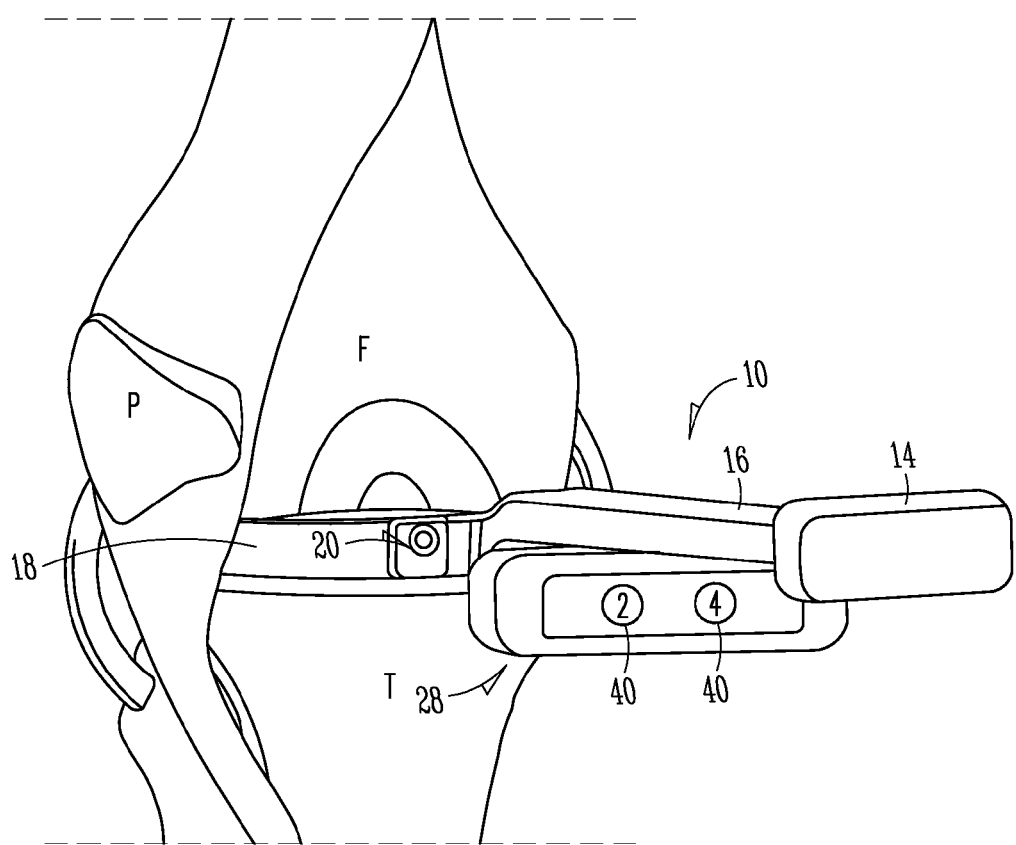
FIG. 21: illustrates a perspective view of a knee balancing system positioned within a gap formed between a cut surface on a distal end of a femur and a cut surface on a proximal end of a tibia, as constructed in accordance with at least one embodiment.

FIG. 21 illustrates a front view of the knee joint, with the system 10 in place within the gap G and before any adjustment has been made to expand the system 10 to increase its collective height. As is evident from this figure and as discussed above, the shaft 16 and the handle 14 of the main body 12 can be offset relative to a center of the platform 18. This offset configuration can allow for easier access to the front of the knee joint for adjustment via the adjustment screw 20. In the example shown, sensed forces on the medial and lateral aspects of the knee joint are currently out of balance and are at a low end of the possible numerical range, as designated by the displayed numbers of 2 and 4, since no height adjustment has been made.

Figure 22:
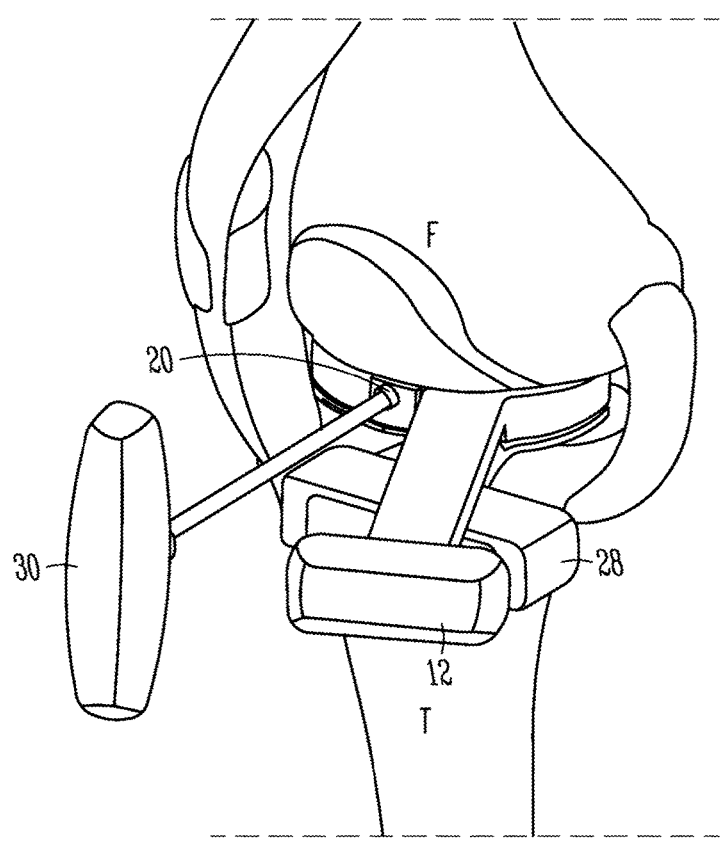
FIG. 22: illustrates an elevation perspective view of adjusting an adjustment mechanism of a knee balancing system to increase or decrease a collective height of the system, as constructed in accordance with at least one embodiment.
Figure 23A:
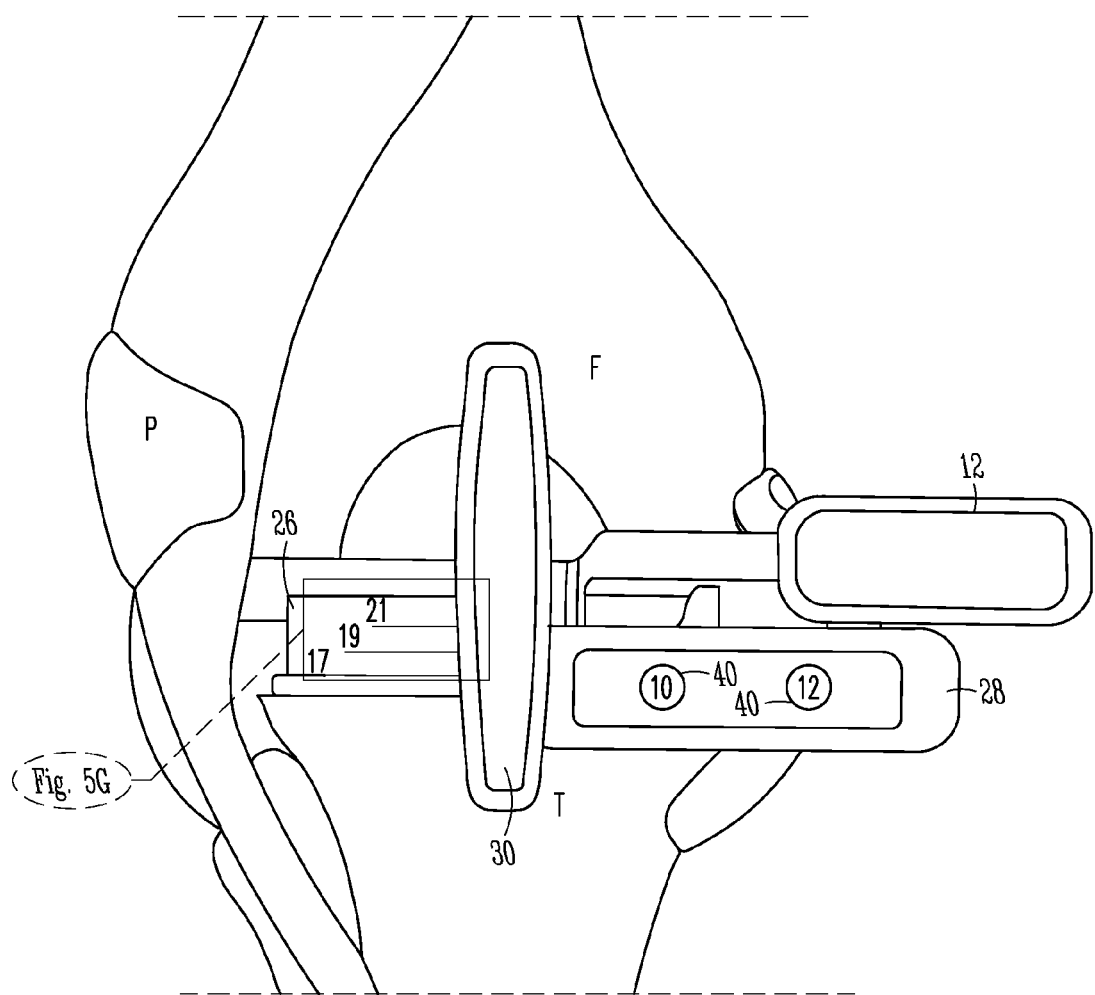
FIG. 23A: illustrates a front perspective view of adjusting an adjustable mechanism of a knee balancing system to increase or decrease a collective height of the system, as constructed in accordance with at least one embodiment.
Figure 23B:
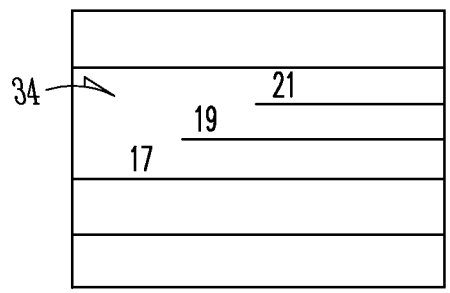
FIG. 23B: illustrates a close-up view of a plurality of distraction height markings of a moveable sensor platform, included in a knee balancing system, as constructed in accordance with at least one embodiment.

FIG. 22 illustrates a perspective view of the knee joint, with the adjustment wrench 30 being used to adjust the system's 10 collective height. After the system 10 is inserted into the knee gap, the adjustment wrench 30 can be used to expand the system's 10 height. In various alternative examples, any suitable adjustment members can be used in place of the adjustment wrench 30, the adjustment screw 20, the adjustment screw capture nut 22 (FIG. 1), and the adjustable wedge 24 (FIG. 1). For example, a screwdriver, a key, a removable dial, a pump with an air bladder, or any of a number of suitable devices can be used for adjusting the collective height of the portions of the system 10 within the knee joint gap G.

FIGS. 23A and 23B again illustrate a front view of the knee joint; this time after the system 10 has been adjusted to increase its collective height. Graduated distraction markings 34 on an outer surface of the moveable sensor platform 26 are now visible, indicating an approximate measurement of the gap G between the cut distal femur F and the cut proximal tibia T (in the example shown, about 21 millimeters). Sensed force has increased on both sides of the knee, relative to FIG. 21, as indicated by the indicator 40 displaying the larger numbers 10 and 12. Typically, the system 10 is adjusted by an attending surgeon or other caregiver until he/she believes that soft tissues around the knee are activated, so that if ligament release(s) is performed, it will affect the numbers displayed on the indicator 40. Alternatively, the attending surgeon or other caregiver can increase the height of the system 10 until a desired reading of force measurement is indicated on the indicator 40.

Figure 24:
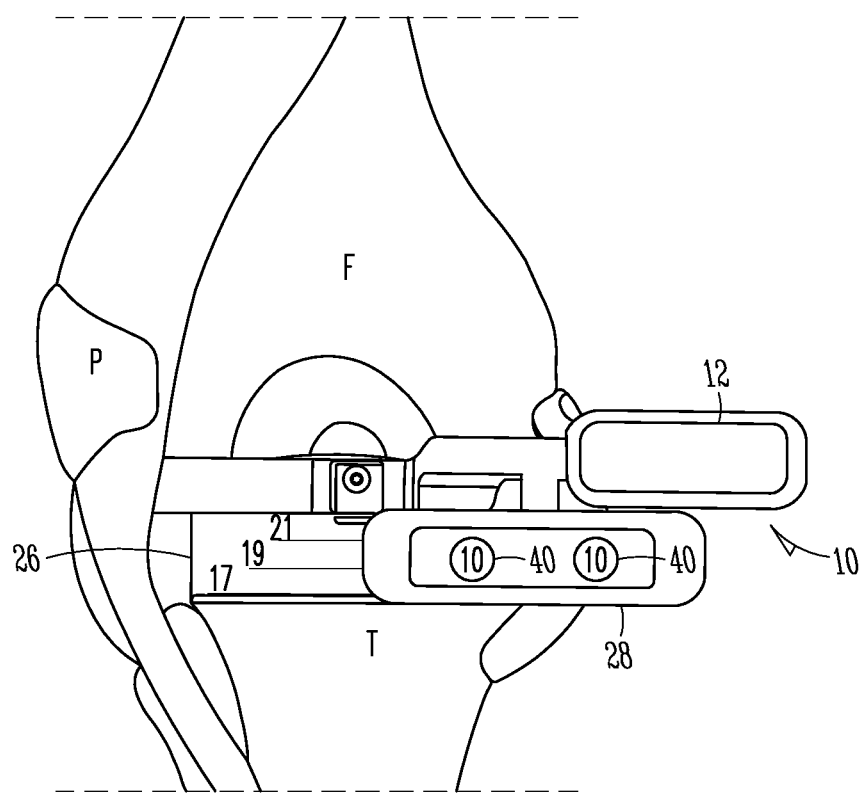
FIG. 24: illustrates a front perspective view of a knee balancing system after ligament release(s) has been performed to balance the medial and lateral forces imposed on the system, as constructed in accordance with at least one embodiment.

FIG. 24 illustrates a front view of the knee joint after ligament release(s) has been performed to balance medial and lateral forces imposed on the system 10. Ligaments can be released on one or both sides of the knee joint to balance tension about the joint and thus the forces sensed by the force sensor 28. The balanced forces are indicated by indicator 40 numerical readings of 10 and 10 on both medial and lateral sides. Now that ligament balancing has been achieved, the system 10 can be removed from the knee joint and the rest of the knee replacement surgical procedure can be performed. In some examples, the system 10 can subsequently be used on the opposite knee.

Closing Notes:

Devices, systems and methods are provided for facilitating knee balancing during a knee replacement surgery. A system can include a force sensor, a main body, a moveable sensor platform, and an adjustment mechanism. The force sensor can sense one or more forces applied within a knee joint, including forces applied on a medial side and a lateral side. The movable sensor platform can be coupled between the force sensor and the main body. The adjustment mechanism can adjust the moveable sensor platform, relative to the main body, thereby adjusting a height of the system. A method can include inserting portions of a knee balancing system into a gap formed between a distal end of a femur and a proximal end of a tibia, adjusting an adjustable mechanism of the knee balancing system to increase or decrease a collective height of the system, and sensing and displaying the medial and lateral forces.

The above Detailed Description includes references to the accompanying drawings, which form a part of the Detailed Description. The drawings show, by way of illustration, specific embodiments in which the present knee balancing devices, systems and methods can be practiced. These embodiments are also referred to herein as "examples."

While certain examples are shown and described with respect to a specific knee (i.e., a left knee or a right knee), it is to be appreciated that the present disclosure is equally applicable to both the left and right knees. All examples can also be configured and used in partial or total knee replacement procedures. It is believed that similar examples can be used with other non-knee areas of orthopedics, which can benefit through distraction from a thin profile, such as but not limited to total disc arthroplasty.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, "anterior" or "front" refers to a direction generally toward the front of a patient, "posterior" or "back" refers to a direction generally toward the back of the patient, "medial" refers to a direction generally toward the middle of the patient, and "lateral" refers to a direction generally toward the side of the patient. In this document, "bottom side" refers to a side of a knee balancing system that faces a proximal tibial surface and "top side" refers to a side of a knee balancing system that faces a distal femoral surface. Notably, the present inventors appreciate that the present knee balancing devices, systems and methods can be configured such that a bottom side in a first embodiment of a knee balancing system can be a top side in a second embodiment of the knee balancing system; similarly, a top side in the first embodiment can be a bottom side in the second embodiment. As such, reference to a bottom side, a top side, or similar should not be viewed as limiting.

In the appended claims, the terms "including" and "in which" are used as the plain-English equivalents of the respective terms "comprising" and "wherein." The terms "including" and "comprising" are open-ended, that is, a system, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A knee balancing system for facilitating a knee arthroplasty procedure, the system comprising:
a force sensor configured to sense one or more forces applied within a knee joint, including a force applied on a medial side of the knee joint and a force applied on a lateral side of the knee joint;
a main body;
a moveable sensor platform positioned between the force sensor and the main body; and
an adjustment mechanism configured to adjust the moveable sensor platform relative to the main body, the adjustment mechanism positioned within the main body and including a linear medial track and a linear lateral track each of the linear medial track and the linear lateral track recessed within a base member portion of the adjustment mechanism and including one or more actuating ramped surfaces in fixed locations along each respective track.

2. The system of claim 1, wherein the force sensor is configured to sense one or more forces applied within the knee joint between a cut distal end of a femur and a cut proximal end of a tibia.

3. The system of claim 1, further including a numerical display, wirelessly or integrally coupled with the force sensor, configured to display a first number representing the force applied on the medial side and a second number representing the force applied on the lateral side.

4. The system of claim 1, wherein movement of the adjustment mechanism results in the moveable sensor platform moving up or down, relative to the main body, to increase or decrease a height of portions of the force sensor that reside within the knee joint, relative to the main body.

5. The system of claim 4, wherein a collective height of portions of the force sensor, the main body, the moveable sensor platform, and the adjustment mechanism is adjustable from about 15 millimeters to about 21 millimeters.

6. The system of claim 1, wherein one or both of the movable sensor platform or the adjustment mechanism includes a plurality of distraction height markings.

7. The system of claim 1, wherein the main body includes:
a platform configured to be inserted into the knee joint and couple with the moveable sensor platform;
a shaft extending from the platform; and
a handle at an end of the shaft, opposite the platform.

8. The system of claim 7, wherein the shaft extends from a location that is offset from a center of the platform.

9. The system of claim 1, wherein the adjustment mechanism includes one or more threaded screws or bolts.

10. The system of claim 9, wherein the adjustment mechanism further includes an adjustable wedge movable within a perimeter of the main body through rotation of the one or more threaded screws or bolts.

11. The system of claim 10, wherein the adjustable wedge includes a base member, one or more plate members, and one or more column members, the one or more plate members movable within the perimeter of the main body through rotation of the one or more threaded screws or bolts.

12. The system of claim 11, wherein the one or more column members move along a first vertical linear direction in response to movement of the one or more plate members along a second horizontal linear direction, which is perpendicular to the first vertical linear direction.

13. The system of claim 9, wherein the adjustment mechanism further includes a screwdriver or a wrench.

14. The system of claim 12, wherein the one or more column members travel within one of the linear medial track and the linear lateral track and engage at least one of the one or more actuating ramp surfaces.

15. The system of claim 1, wherein the moveable sensor platform includes one or more actuating ramped surfaces that engage with the one or more actuating ramped surfaces of the adjustment mechanism.

16. A method for facilitating balancing tension applied to a knee joint by one or more ligaments or other soft tissue during a knee arthroplasty procedure, the method comprising:
inserting portions of a knee balancing system, including a force sensor, a main body, a movable sensor platform positioned between the force sensor and the main body, and an adjustment mechanism located within the main body, into a gap formed between a distal end of a femur and a proximal end of a tibia;
adjusting the adjustable mechanism of the knee balancing system to cause sliding engagement between one or more column elements and one or more actuating ramped surfaces in fixed locations within a linear medial track and a linear lateral track each track recessed within a base member portion within the adjustable mechanism to produce an increase or decrease a collective height of the system, including moving the moveable sensor platform and the force sensor relative to the main body;
sensing, using the force sensor, an amount of medial force applied against a medial portion of the knee balancing system by the femur and the tibia and an amount of lateral force applied against a lateral portion of the knee balancing system by the femur and the tibia; and
displaying the amounts of medial and lateral force on the knee balancing system.

17. The method of claim 16, further comprising releasing at least one ligament or soft tissue structure of the knee joint based on the displayed amounts of medial and lateral force.

18. The method of claim 16, wherein inserting portions of the knee balancing system into the gap formed between the distal end of the femur and the proximal end of the tibia includes inserting portions of the knee balancing system between a cut surface of the distal end of the femur and a cut surface of the proximal end of the tibia.

19. The method of claim 16, wherein adjusting the adjustable mechanism of the knee balancing system includes increasing the collective height of the system from about 15 millimeters to at least about 17 millimeters.

20. The method of claim 16, wherein adjusting the adjustable mechanism of the knee balancing system includes engaging one or more threads of a screw or a bolt coupled to a plate member adapted to traverse in a horizontal linear direction in response to movement of the one or more threads of the screw.

21. The method of claim 20, wherein engaging the one or more threads of the screw or the bolt with the adjustable wedge includes turning a screwdriver or a wrench coupled with the screw or the bolt to move the plate member in a horizontal linear direction; and
wherein the plate member is adapted to engage the one or more column elements which move in both a vertical linear direction and a horizontal linear direction in response to turning the screwdriver or the wrench.

22. The method of claim 16, wherein adjusting the adjustable mechanism of the knee balancing system includes engaging one or more threads of a first screw or first bolt with a first plate member and engaging one or more threads of a second screw or second bolt with a second plate member;

wherein the first plate member is adapted to engage at least a first column element of the one or more column elements, the first column element adapted to move in both a vertical and a horizontal linear direction in response to turning the first screw or the first bolt; and wherein the second plate member is adapted to engage at least a second column element of the one or more column elements, the second column element adapted to move in both a vertical and a horizontal linear direction in response to turning the second screw or the second bolt.

23. The method of claim 22, wherein engaging the one or more threads of the first screw or first bolt with the first plate member includes adjusting the collective height of the medial portion of the knee balancing system, and wherein engaging the one or more threads of the second screw or second bolt with the second plate member includes adjusting the collective height of the lateral portion of the knee balancing system.

24. The method of claim 16, wherein displaying the amounts of medial and lateral force includes displaying a first numerical value representing an amount of force applied against the medial portion of the knee balancing system and a second numerical value representing an amount of force applied against the lateral portion of the knee balancing system.

* * * * *